United States Patent [19]

Felix et al.

[11] 4,078,049

[45] Mar. 7, 1978

[54] ACETYLCHOLINE ASSAY

[75] Inventors: Arthur Martin Felix, West Caldwell; Sidney Spector, Livingston, both of N.J.

[73] Assignee: Hoffmann-La Roche Inc., Nutley, N.J.

[21] Appl. No.: 773,024

[22] Filed: Feb. 28, 1977

[51] Int. Cl.$^2$ .................... G01N 33/16; A61K 39/00; A61K 43/00
[52] U.S. Cl. .................................. 424/1; 260/112 R; 424/12
[58] Field of Search ................ 260/112 R; 424/1, 1.5, 424/12; 23/230 B

[56] References Cited
PUBLICATIONS

Almon et al., Chemical Abstracts, vol. 84, No. 17, Apr. 26, 1976, p. 362, Abstract No. 119550d.

*Primary Examiner*—Benjamin R. Padgett
*Assistant Examiner*—Christine M. Nucker
*Attorney, Agent, or Firm*—Samuel L. Welt; George M. Gould; Raymond R. Wittekind

[57] ABSTRACT

A sensitive immunoassay for acetylcholine is described. To prepare the acetylcholine selective antiserum, an antigen is made comprising 6-aminocaproic acid (2-trimethylaminoethyl) ester covalently bonded to an immunogenic carrier material through a peptide bond formed from said 6-amino group and carboxyl groups contained in said immunogenic carrier material and the antigen is injected into a suitable host animal to elicit the desired antiserum.

7 Claims, No Drawings

ACETYLCHOLINE ASSAY

BACKGROUND OF THE INVENTION

Antibody to the acetylcholine receptor has been observed in patients with myasthenia gravis. The determination of such antibody has been suggested as diagnostic test for myasthenia gravis. See Lindstrom et al., Neurology, 26, 1054 (1976) and reference cited therein.

DESCRIPTION OF THE INVENTION

The present invention relates in one aspect to a novel antigen useful in eliciting antiserum selective to acetylcholine. The antigen comprises 6-aminocaproic acid (2-trimethylaminoethyl) ester covalently bonded to an immunogenic carrier material through a peptide bond formed from the 6-amino group of the hapten and carboxyl groups contained is said immunogenic carrier material.

As used herein the term "immunogenic carrier material" is meant to include those materials which have the property of independently eliciting an immunogenic response in a host animal when injected therein and which can be coupled by covalent bonding to said hapten. Suitable carrier materials include, for example, materials such as proteins, natural or synthetic polymeric compounds such as polypeptides, e.g., polylysine; polysaccharides; and the like. A particularly preferred carrier material for the practice of the present invention is protein.

The identity of the protein carrier material utilized in the preparation of the instant antigen is not narrowly critical. Example of preferred proteins useful in the practice of this invention include the serum proteins preferably mammalian serum proteins, such as, for example, human gamma globulin, human serum albumin, rabbit serum albumin, bovine gamma globulin and bovine serum albumin. Other suitable protein products will be suggested to one skilled in the art. It is generally preferred that proteins be utilized which are foreign to the animal host in which the resulting antigen will be employed.

A further aspect of the present invention relates to the novel hapten 6-aminocaproic acid (2-trimethylaminoethyl) ester. This compound is conveniently prepared by a multi-step synthesis from the known starting material 6-aminocaproic acid.

In a first step of such synthesis the amino moiety is converted to a protecting form using, agents conventionally employed in peptide chemistry to protect side chain amino groups. Suitable protecting groups useful in the present invention include benzyloxycarbonyl, t-butyloxycarbonyl, biphenylisopropyloxycarbonyl and the like. Reagents and conditions useful in introducing the N-protecting group onto the starting compound are well known in the art. A preferred protecting group is benzyloxycarbonyl which is conveniently introduced by reacting 6-aminocaproic with a benzyloxycarbonyl halide preferably benzyloxycarbonyl chloride, in dilute base, i.e., sodium hydroxide at a temperature in the range of from about $-15°$ to $25°$ C, preferably at about $0°$ C.

The product 6-N-protected aminocaproic acid is then treated with a $\beta$-dimethylaminoethyl halide, preferably the chloride in an inert organic solvent such as a lower alkanoic acid lower alkyl ester, i.e., ethyl acetate, in the presence of a tertiary alkyl amine such as triethylamine. The reaction is carried out at an elevated temperature, preferably at the reflux temperature of the reaction mixture and yields a 6-N-protected aminocaproic acid (2-dimethylaminoethyl) ester.

The aforesaid ester compound is then reacted with a lower alkyl p-toluenesulfonate, preferably methyl p-toluenesulfonate in an inert organic solvent such as ethyl acetate at a temperature in the range of from $0°$ to $50°$ C, preferably at about room temperature. There is thus produced a 6-N-protected aminocaproic acid (2-trimethylamino ethyl) ester p-toluenesulfonate.

In a further process step of the present synthesis, the 6-N-protected aminocaproic aicd (2-trimethylaminoethyl) ester p-toluenesulfonate prepared as above is treated with a strong acid or acid mixture to selectively cleave the protecting group. Thus when the N-protecting group is benzyloxycarbonyl, cleavage is achieved by use of a trifluoracetic acid-hydrogen bromide treatment initially at low temperatures, i.e., $-20°$ to $10°$ C, preferably about $0°$ C, followed by continued treatment at a somewhat higher temperature such as in the range of from $10°$ to $50°$ C, preferably at about $25°$ C. The resulting 6-aminocaproic acid (2-trimethylaminoethyl) ester p-toluenesulfonate is obtained in the form of its acid addition salt, that is as the hydrobromide. Obviously, if other protecting groups have been employed in the synthesis, then conditions and reagents used for cleavage will be those conventionally employed in the art for the respective groups and the resulting product will be in the form of the acid addition salt of the reagent acid used in the cleavage procedure.

The hapten so obtained can then be coupled to the immunogenic carrier material by any of the procedures known in the art for this purpose. One preferred method is to directly couple the hapten to the immunogenic carrier material using a water soluble carbodiimide coupling reagent. A preferred carbodiimide coupling reagent is 1-ethyl-3-(3-dimethylaminopropyl)carbodiimide. The coupling reaction to prepare the antigen is carried out in aqueous medium at a pH in the range of about 4 to 8, preferably at a pH of about 5.5.

The antigen of the present invention may then be utilized to induce formation of acetylcholine specific antibodies in the serum of host animals by injecting the antigen in such host repeatedly over a period of time. The collected serum may be used per se as an acetylcholine specific antiserum or, if desired, the antibodies therein may be further purified by precipitation with a neutral salt solution followed by dialysis and column chromatography.

Suitable host animals for preparing antiserum to acetylcholine include mammals such as rabbits, horses, goats, guinea pigs, rats, cows, sheep and the like. The resulting antibodies will have a multiplicity of active sites which will selectively complex with acetylcholine and the antigen of the present invention.

The formation of acetylcholine specific antibodies in the host animals may be monitored by taking blood samples from the host animal and adding it to an amount of the labelled hapten. The presence of a labelled hapten-antibody complex indicates antibody activity. The antigen treatment of the animal can be continued until the antibody titre reaches a desired level of activity. For the purpose of this application the antibody titre is defined as being the maximum dilution of the antibody to precipitate 50% of the added labelled hapten.

The specific antibodies of the present invention are useful as reagents in biochemical assays for the determination of the presence of acetylcholine in biological fluids such as plasma, urine and tissue extracts. The concentration of acetylcholine in biological fluids, the neurotransmitter for the cholinergic nervous system, is altered in some neuromuscular disease states, for example, myasthemia graves. A particularly preferred assay procedure is the radioimmunoassay procedure such as described in U.S. Pat. No. 3,709,868. Preferred labelled acetylcholine for use in immunoassay include isotopically labelled acetylcholine, particularly acetylcholine —$H^3$ or —$C^{14}$ as well as acetylcholine labelled with an electron spin resonance group. Examples of the use of various electron spin resonance labelled molecules in bioassays are to be found in U.S. Pat. Nos. 3,453,288, 3,481,952 and 3,507,876.

The radioimmunoassay method is preferred for the determination of acetylcholine. It is a sensitive, simple and rapid procedure. Thus it is possible to determine as little as 300 pg of acetylcholine in tissue using 50 mg sample.

EXAMPLE 1

N-Benzyloxycarbonyl-6-aminocaproic acid

A solution of 6-aminocaproic acid (13.1 g, 0.10 mole) in 2.5 N NaOH (40 ml, 0.10 mole) was cooled to 0° and benzyloxycarbonyl chloride (18.7 g, 0.11 mole) in ether (25 ml and 2.5N NaOH (50 ml, 0.125 mole) were added simultaneously in several portions, with vigorous stirring, over a 1 hr period. The reaction mixture was extracted with ether (3 × 50 ml), cooled in an ice-bath and acidified with 6M HCl. The crystalline product was recrystallized from ether-pet ether to give 19.4 g of product (73.2%); mp 54°–55.5°.

EXAMPLE 2

6-Benzyloxycarbonyl-aminocaproic acid (2-dimethylaminoethyl) ester

A solution of N-benzyloxycarbonyl-6-aminocaproic acid, (2.65 g, 0.010 mole) in ethyl acetate (60 ml) was treated with triethylamine (2.8 ml, 0.020 mole) and 1.48M β-dimethylaminoethyl chloride (17 ml, 0.025 mole) and refluxed for 16 hrs. The reaction mixture was filtered and the filtrate extracted with saturated NaCl (3 × 50 ml), 5% $NaHCO_3$ (3 × 50 ml), saturated NaCl (3 × 50 ml), dried over $MgSO_4$, filtered and evaporated to dryness. The product was obtained as a viscous oil, 1.55 g (46.1%).

Anal. calcd for $C_{18}H_{28}N_2O_4$: C, 64.26; H, 8.39; N, 8.33. Found: C, 63.98; H, 8.51; N, 8.37.

EXAMPLE 3

6-Benzyloxycarbonyl-aminocaproic acid (2-trimethylaminoethyl) ester p-toluenesulfonate A solution of N-benzyloxycarbonyl-6-aminocaproic acid (2-dimethylaminoethyl) ester, (1.5 g, 4.46 mmole) in ethyl acetate (10 ml) was treated with methyl p-toluenesulfonate (831 mg, 4.46 mmole). After standing at 25° for 3 hours the product precipitated, 1.91 g (82.0%). Recrystallization from ethanol-ether gave white crystalline product, mp 105°–106.5°.

Anal. calcd for $C_{26}H_{38}N_2O_7S$: C, 59.75; H, 7.33; N, 5.36; S, 6.13. Found: C, 59.70; H, 7.25; N, 5.28; S, 6.14.

EXAMPLE 4

6-Aminocaproic acid (2-trimethylaminoethyl) ester p-toluenesulfonate hydrobromide N-Benzyloxycarbonyl-6-aminocapric acid (2-trimethylaminoethyl) ester p-toluenesulfonate, (1.7 g, 3.25 mmole) was dissolved in trifluoroacetic acid (25 ml) and hydrogen bromide was passed through the solution at 0° for 45 minutes and 25° for 30 minutes. The solution was evaporated to dryness and the residue crystallized from ethanol-ether to give 1.25 g (81.7%). Recrystallization from DMF-ether afforded white crystalline product, mp 139.5°–143°.

Anal. calcd for $C_{18}H_{32}N_2O_5S.HBr$: C, 46.05; H, 7.08; N, 5.97; Br, 17.02. Found: C, 45.77; H, 7.30; N, 5.95; Br, 17.84.

EXAMPLE 5

Attachment of 6-aminocaproic acid (2-trimethylaminoethyl) ester p-toluenesulfonate to bovine serum albumin A mixture of 6-aminocaproic acid (2-trimethylaminoethyl) ester p-toluenesulfonate hydrobromide, (94 mg, 0.20 mmole) and bovine serum albumin (25 mg) in $H_2O$ (3.0 ml) was adjusted to pH 5.5. 1-Ethyl-3(3-dimethylaminopropyl)-carbodiimide (38 mg, 0.20 mmole) was added and the reaction proceeded at 25° for 2 days. The solution was transferred into Spectrapor No. 2 dialysis tubing, dialyzed against water for 3½ days and freeze dried to afford 20.7 mg of product.

EXAMPLE 6

Immunization with 6-aminocaproic acid (2-trimethylaminoethyl) ester p-toluene sulfonate bovine serum albumin conjugate New Zealand albino rabbits were immunized with 6-aminocaproic acid (2-trimethylaminoethyl) ester p-toluene sulfonate bovine serum albumin conjugate from Example 5 once a week for 3 weeks and then once every 2 to 4 weeks. The immunogen (1 mg) was dissolved in phosphate-buffered saline (pH 7.4) (1 ml) and emulsified with complete Freund's adjuvant (1 ml). The emulsion (1 ml) was injected into the four foot pads (0.25 ml/pad). Bleedings were taken from the central ear artery 2 weeks after the last booster immunization. The blood was allowed to clot overnight at 4° C and then centifuged at 2,000 rpm for 15 minutes to separate serum.

EXAMPLE 7

Radioimmunoassay with antisera to acetyl choline bovine serum albumin conjugate

The antiserum of Example 6 as used for the radioimmunoassay was diluted with normal rabbit serum which was diluted with phosphate-buffered saline, pH 7.4, at 1:10 -dilution. To determine the antibody titre of antiserum, 0.1 ml of various dilutions of the antiserum was incubated in an assay tube (10 × 75 mm) with 2 mg of acetylcholine — $H^3$ approximately 3,000 cpm at 4° C for 2 hours. A total of 50 ul of eserine ($10^{-3}M$) was added to inhibit acetylcholinesterase. The volume was adjusted to 0.5 ml with phosphate-buffered saline, pH 7.4, which is the optimal pH for the assay. The antibody bound acetylcholine was separated from free acetylcholine by the addition of saturated ammonium sulfate which was adjusted to pH 7.4 with ammonium hydroxide as described by Farr, J. Infect. Dis. 103, 239 (1958). After 2 washings with 50% saturated ammonium sulfate, the precipitate was dissolved in 0.5 ml of water. The content of the tube was transferred to counting vial and the tube was then washed four times with 3 ml of Riaflour. The 12 ml washings were all collected in the vial. The radioactivity was then counted with a Beckman liquid scintillation counter. The dilution of the antiserum chosen for further studies was 1:50.

Appropriate volume of phosphate-buffered saline, pH 7.4 was added to all tubes containing 0.1 ml of the antiserum and 50 ul of eserine ($10^{-3}$M) to make a final incubation volume of 0.5 ml. To the tubes were added 100 ul of acetylcholine —$H^3$ and various quantities ranging from 100 ng to 500 pg of acetylcholine, choline or acetate. The tubes were then incubated for 2 hours at 4° C followed by precipitation with ammonium sulfate.

A standard curve for plasma was obtained by adding known amounts of acetylcholine in 10 ul of normal rabbit plasma to the assay tubes by adjusting the volume to 0.5 ml with phosphate-buffered soline, pH 7.4.

A computer program was utilized to obtain the standard curves.

RESULTS

Sensitivity of the radioimmunoassay

The antibody of the sera of rabbits immunized with the acetylcholine bovine serum albumin immunogen was determined by the binding of acetylcholine —$H^3$. Ouchterlony long plates also indicated the presence of the antibody in sera of rabbits immunized with the congugated acetylcholine. As little as 10 pg of acetylcholine can be detected by the antiserum of a rabbit immunized with 6-aminocaproic acid (2-trimethylaminoethyl) ester p-toluene sulfonate bovine serum albumin immunogen. The assay is linear up to 100 ng.

Specificity of the radioimmunoassay

The specificity of the antibody in the antiserum of rabbit immunized by the acetylcholine bovine serum albumin immunogen was determined by incubating the antiserum with acetate or choline in the presence of labelled acetylcholine. Acetylcholine produced a 50% inhibition of binding of acetylcholine —$H^3$ to the antibody at a concentration of 0.03 nM. The antibody failed to recognize acetate. In order to obtain a acetylcholine —$H^3$ antibody complex formation, concentrations of choline of about $3 \times 10^3$ times that of acetylcholine are required.

We claim:

1. An antigen consisting essentially of a hapten, 6-aminocaproic acid (2-trimethylaminoethyl) ester and acid addition salts thereof, covalently bonded to an immunogenic carrier material through peptide bonds formed between said 6-amino group and carboxyl groups on said immunogenic carrier material.

2. The antigen of claim 1 wherein said immunogenic carrier material is bovine serum albumin.

3. The antigen of claim 1 wherein said hapten is 6-aminocaproic acid (2-trimethylaminoethyl) ester p-toluenesulfonate hydrogen bromide.

4. An antibody specific to acetylcholine prepared by innoculating a host animal with an antigen consisting essentially of a hapten, 6-aminocaproic acid (2-trimethylaminoethyl) ester and acid addition salts thereof, covalently bonded to an immunogenic carrier material through peptide bonds formed between said 6-amino group and carboxyl groups on said immunogenic carrier material and collecting the serum from said host animal.

5. The antibody of claim 4 wherein said antigen consists essentially of 6-aminocaproic acid (2-trimethylaminoethyl) ester p-toluenesulfonate hydrogen bromide covalently bonded to bovine serum albumin.

6. A method for the assay of acetylcholine in a sample, which method comprises mixing said sample with a known amount of labelled acetylcholine and an antibody which will selectively complex with acetylcholine, measuring the degree of binding of said labelled acetylcholine compound with said antibody, and determining the amount of acetylcholine present in said sample by comparing said degree of binding to a standard curve obtained by mixing known amounts of acetylcholine with fixed amounts of said labelled acetylcholine and said antibody and determining the degree of binding for each known amount of acetylcholine.

7. The method of claim 6 wherein said labelled acetylcholine is acetylcholine-$^3$H.

* * * * *